(12) United States Patent
Kimura et al.

(10) Patent No.: US 7,497,129 B2
(45) Date of Patent: Mar. 3, 2009

(54) RUBBER SPECIMEN-STRETCHING JIG AND APPARATUS AND METHOD FOR ANALYZING MOLECULAR STRUCTURE AND MOLECULAR MOTION OF STRETCHED RUBBER SPECIMEN

(75) Inventors: Hideaki Kimura, Hyogo (JP); Marina Kotani, Hyogo (JP); Hidehiko Dohi, Hyogo (JP)

(73) Assignee: Sumitomo Rubber Industries, Ltd., Kobe (JP)

( * ) Notice: Subject to any disclaimer, the term of this patent is extended or adjusted under 35 U.S.C. 154(b) by 219 days.

(21) Appl. No.: 11/705,781

(22) Filed: Feb. 14, 2007

(65) Prior Publication Data

US 2007/0186675 A1 Aug. 16, 2007

(30) Foreign Application Priority Data

Feb. 15, 2006 (JP) ............................. 2006-038544

(51) Int. Cl.
*G01N 3/24* (2006.01)
(52) U.S. Cl. ........................................................ 73/842
(58) Field of Classification Search ................... 73/842
See application file for complete search history.

(56) References Cited

U.S. PATENT DOCUMENTS 4,574,046 A * 3/1986 Sprow .......................... 209/44
6,141,865 A * 11/2000 Kakutani et al. .............. 29/733

OTHER PUBLICATIONS

"Processing of Polymer," vol. 53, No. 3, (2004), pp. 102-107.

* cited by examiner

*Primary Examiner*—Harshad Patel
*Assistant Examiner*—Octavia Davis
(74) *Attorney, Agent, or Firm*—Birch, Stewart, Kolasch & Birch, LLP

(57) ABSTRACT

A rubber specimen-stretching jig including a jig body has a disk-shaped pedestal; a columnar rubber specimen-fitting support erected on the pedestal; and a columnar retaining ring-fitting support projected from an upper end surface of the rubber specimen-fitting support; and an annular retaining ring removably fixedly fitted around the retaining ring-fitting support.

The jig body is inserted into the cylindrical rotor, with one or more stretched annular rubber specimens wound around the rubber specimen-fitting support of the jig body; and with an inner surface of the rotor fixedly pressed against an outer surface of the pedestal and that of the retaining ring and brought into contact with the annular rubber specimens, a solid NMR of each of the annular rubber specimens is measured while the stretched annular rubber specimens are being rotated at a high speed by interlocking the stretched annular rubber specimens to the rotor rotated at a high speed.

7 Claims, 6 Drawing Sheets

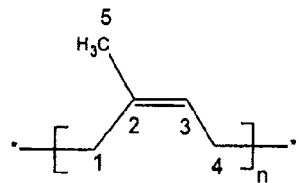
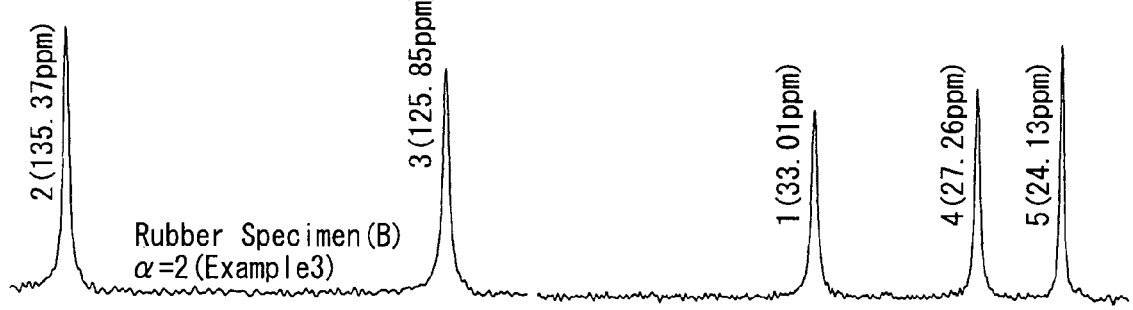
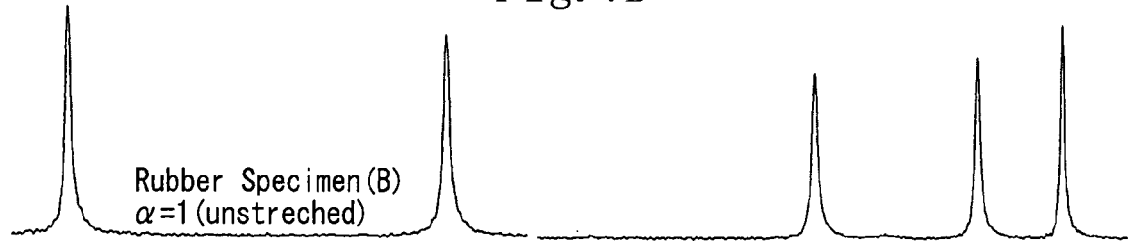
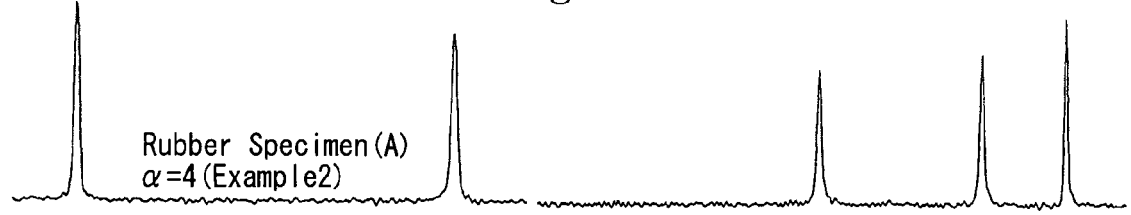
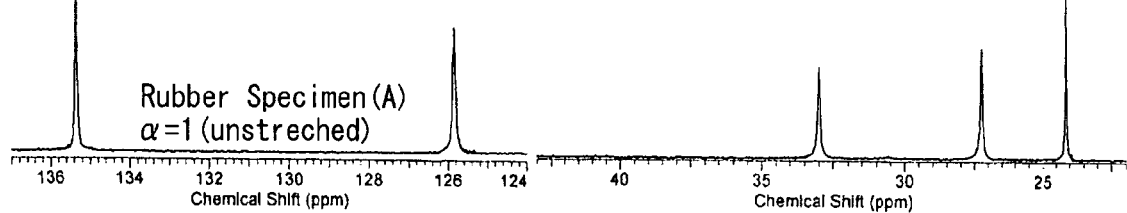
Fig. 7E, 7D, 7C, 7B, 7A

[Prior Art]

US 7,497,129 B2

RUBBER SPECIMEN-STRETCHING JIG AND APPARATUS AND METHOD FOR ANALYZING MOLECULAR STRUCTURE AND MOLECULAR MOTION OF STRETCHED RUBBER SPECIMEN

This nonprovisional application claims priority under 35 U.S.C. § 119(a) on Patent Application No(s). 2006-038544 filed in Japan on Feb. 15, 2006, the entire contents of which are hereby incorporated by reference.

BACKGROUND OF THE INVENTION

1. Field of the Invention

The present invention relates to a rubber specimen-stretching jig, an apparatus for analyzing the molecular structure and molecular motion of a stretched rubber specimen, and a method for analyzing the molecular structure and molecular motion of the stretched rubber specimen. More particularly, the present invention is intended to detect a solid high-resolution NMR spectrum of the stretched rubber specimen by rotating it at a magic angle (MAS) so that the molecular structure and molecular motion of the stretched rubber specimen are analyzed.

2. Description of the Related Art

In the development of a rubber product, it is very important to select a rubber material having properties suitable for the rubber product by beforehand analyzing the properties of rubber generated, when the component of the rubber material of the rubber product and the mixing amount of the rubber material are changed. For example, a tire made of the rubber material is demanded to have a contradictory performance that both a rolling resistance and gripping performance thereof are compatible with each other. From the standpoint of satisfying this demand to some extent, it is necessary to analyze properties generated when the rubber material is rotated at a high speed, with the rubber material being stretched.

It is indispensable to know the relationship between the elasticity of rubber and the molecular structure thereof in improving and developing the rubber material. In recent years, the development of the rubber material aimed at revealing novel properties and functions thereof based on a nano-level structure is energetically made.

As explanation of the molecular structure of the revelation of the rubber elasticity, the theory that "The rubber deforms affinely", namely, the theory that "A deformation of a polymer chain and a macroscopic stretching thereof are proportional to each other" has been widely accepted. But in recent years, reported are many phenomena which cannot be explained by the affine deformation that "The degree of strain of a rubber matrix induced when a rubber material is stretched is not uniform, and when a considerably large load is applied thereto in one direction, 75% of a polymer chain does not orient". Thus it is now necessary to re-examine the relationship between the rubber elasticity and the molecular structure. To this end, it is necessary to directly observe the molecular structure and molecular motion of the stretched rubber material.

Such being the case, the following apparatus 6 (non-patent document 1) shown in FIG. 8 is proposed. The apparatus is developed to measure a solid 13CNMR of natural rubber when it is tensioned to thereby analyze the molecular structure and molecular motion of the natural rubber when it is tensioned. In the apparatus 6, with both ends of the natural rubber specimen 1 fixed with the wire 2 having a high strength and magnetism. With the specimen 1 being stretched in parallel with the external magnetic field BO by the stretching device 3 fixed to one end of the wire 2, the NMR signal is detected by the saddle-type coil 5, surrounding the specimen 1, which is disposed inside the probe 4 to thereby obtain the solid 13CNMR spectrum.

Because the NMR spectrum of the solid specimen has a very large line width owing to a chemical shift anisotropy of the specimen and an interaction of dipoles, it is impossible to separate signal peaks at respective portions of molecules to be measured. Therefore it is difficult to analyze the structure of the molecules. In relation to this problem, it is known that an anisotropic interaction is removed owing to a magic-angle rotation (MAS) accomplished by a rotation of a specimen tube at a high speed not less than several kHz, with the specimen tube inclined at a certain angle (54.7°) to the static magnetic field BO. Thereby a high-resolution NMR spectrum having a sharp peak is obtained.

In a conventional art shown in FIG. 9, a solid specimen is charged into a cylindrical rotor 7 open at its upper portion. A cap 8 having a blade portion formed thereon is inserted into the rotor 7 by press fit. The cap-mounted rotor 7 is disposed inside a probe (not shown) for rotating the specimen at the magic angle. A gas jetted from a nozzle of a stator (not shown) surrounding the rotor 7 is exerted on the blade portion of the cap 8 to allow the magic rotation (MAS) to be accomplished by rotating the rotor 7 at a high speed.

In the measurement of the solid 13CNMR by using the apparatus disclosed in the non-patent document 1, because the rubber specimen 1 is fixed in a vertically stretched state, it is impossible to measure the solid 13CNMR of the rubber specimen 1 while the rubber specimen 1 is rotating at a high speed. Thus it is difficult to obtain the high-resolution NMR spectrum having a sharp peak. Further because the rubber specimen 1 is fixed in the air, it is impossible to achieve a correct temperature-variable measurement.

In the measurement of the solid 13CNMR to be made by rotating the specimen at the magic angle (MAS), when the specimen is charged nonuniformly inside the rotor 7, the specimen has an unfavorable balance and cannot be rotated at a high speed. Thus it is necessary to uniformly charge the specimen inside the rotor 7. But it is very difficult to uniformly charge the rubber specimen inside the rotor 7 with the rubber specimen stretched.

Non-patent document 1: "Processing of polymer", third issue of 53 volume (2004) at pages 102 through 107

SUMMARY OF THE INVENTION

The present invention has been made to solve the above-described problems. Therefore it is an object of the present invention to provide a rubber specimen-stretching jig capable of detecting a solid high-resolution NMR spectrum by allowing a rubber specimen to rotate at a magic angle (MAS) with the rubber specimen stretched and accomplishing a correct temperature-variable measurement so that the molecular structure and molecular motion of the stretched rubber specimen can be analyzed; and a method and an apparatus for analyzing the molecular structure and molecular motion of the stretched rubber specimen.

To achieve the above-described object, the first invention provides a rubber specimen-stretching jig including a jig body having a disk-shaped pedestal; a columnar rubber specimen-fitting support, erected on the pedestal, whose diameter is smaller than that of the pedestal; and a columnar retaining ring-fitting support, projected from an upper end surface of the rubber specimen-fitting support, whose diameter is smaller than that of the rubber specimen-fitting support; and an annular retaining ring removably fixedly fitted around the retaining ring-fitting support.

In this construction, the jig body is inserted into the cylindrical rotor, with one or more stretched annular rubber specimens wound around the rubber specimen-fitting support of the jig body; and with an inner surface of the rotor fixedly pressed against an outer surface of the pedestal and that of the retaining ring and brought into contact with the annular rubber specimens, a solid NMR of each of the annular rubber specimens is measured while the stretched annular rubber specimens are being rotated at a high speed by interlocking the stretched annular rubber specimens to the rotor rotated at a high speed.

As described above, by so constructing the rubber specimen-stretching jig that both the outer surface of the disk-shaped pedestal constructing the jig body and the outer surface of the annular retaining ring fitted around the retaining ring-fitting support also constructing the jig body are fixedly pressed against the inner surface of the rotor, it is possible to rotate the rubber specimen-stretching jig at a high speed by interlocking the rubber specimen-stretching jig to the rotor rotating at a high speed. Further by fixedly pressing the jig against the rotor at upper and lower positions thereof, it is possible to restrain the rubber specimen-stretching jig from whirling, even though it rotates at a high speed.

Further the annular rubber specimen can be stably rotated at a high speed by bringing the outer surface of the annular rubber specimen wound around the rubber specimen-fitting support into contact with the inner surface of the rotor.

Before the jig body is inserted into the rotor, by merely winding the annular rubber specimens around the columnar rubber specimen-fitting support erected on the pedestal with the annular rubber specimens being stretched, the annular rubber specimens can be rotated. That is, by merely mounting the annular rubber specimens around the rubber specimen-fitting support, with an operator stretching the annular rubber specimens, the annular rubber specimens can be rotated in a favorable balance at a high speed, with the annular rubber specimens being stretched uniformly in a rotational direction thereof.

Further according to the above-described construction, because the annular rubber specimen wound around the rubber specimen-fitting support can be held inside the sealed rotor, it is possible to accomplish a correct temperature-variable measurement by controlling the temperature inside the rotor.

It is preferable that the annular rubber specimens wound around the rubber specimen-fitting support are formed as concentric circles and have sectional outer configurations as close to a perfect circle as possible. The number of the annular rubber specimens may be single or plural. For example, by measuring the solid NMR, with a plurality of the same annular rubber specimens wound around the rubber specimen-fitting support, it is possible to obtain an average solid NMR spectrum of all the stretched annular rubber specimens in a short period of time.

The number of the annular rubber specimens which can be wound around the rubber specimen-fitting support is different in dependence on the length of the rubber specimen-fitting support and the number of the annular rubber specimens to be wound around it. For example, when each of the annular rubber specimens is wound singly around the rubber specimen-fitting support and when the rotor having an outer diameter of 7 mm are used, it is preferable to set the number of the annular rubber specimens to be wound around the rubber specimen-fitting support to 1 to 50.

Because the annular rubber specimen is wound around the rubber specimen-fitting support, with the annular rubber specimen being stretched, the inner diameter of the annular rubber specimen in an unstretched original state is set smaller than the diameter of the rubber specimen-fitting support.

By setting the diameter of the rubber specimen-fitting support smaller than that of the pedestal, it is possible to securely obtain an annular rubber specimen-winding space between the outer surface of the rubber specimen-fitting support and the inner surface of the rotor. Further by setting the diameter of the retaining ring-fitting support smaller than that of the rubber specimen-fitting support, it is possible to stably hold the retaining ring on the upper end surface of the rubber specimen-fitting support without the retaining ring slipping downward therefrom.

It is preferable that the diameter of the rubber specimen-fitting support is set to 40 to 90% of the diameter of the pedestal. If the diameter of the rubber specimen-fitting support is below 40% of the diameter of the pedestal, it may be difficult to contact the outer surface of the annular rubber specimen wound around the rubber specimen-fitting support with the inner surface of the rotor. On the other hand, if the diameter of the rubber specimen-fitting support exceeds 90% of the diameter of the pedestal, the space between the outer surface of the rubber specimen-fitting support and the inner surface of the rotor is so small that there is a fear that the annular rubber specimen cannot be held inside the rotor with the annular rubber specimen wound around the rubber specimen-fitting support or that a correct NMR spectrum of the elongated rubber specimen cannot be obtained because the rotor presses the annular rubber specimen excessively, even though the annular rubber specimen is accommodated inside the rotor.

It is preferable that the diameter of the retaining ring-fitting support is 10 to 90% of the diameter of the rubber specimen-fitting support. If the diameter of the retaining ring-fitting support is below 10% of the diameter of the rubber specimen-fitting support, there is a fear that the retaining ring-fitting support has a low strength. On the other hand, if the diameter of the retaining ring-fitting support exceeds 90% of the diameter of the rubber specimen-fitting support, it is difficult to hold the retaining ring on the upper end surface of the rubber specimen-fitting support.

The outer diameter of the pedestal and the outer diameter of the retaining ring are set almost equal to the inner diameter of the rotor so that the pedestal and the retaining ring are fixedly pressed against the inner surface of the rotor. The inner diameter of the retaining ring is set almost equally to the diameter of the retaining ring-fitting support so that the retaining ring is fixedly fitted on the retaining ring-fitting support.

The height of the rubber specimen-stretching jig is not limited to a specific height so long as it can accommodated inside the rotor and an open portion of the rotor can be closed with a cap. But it is preferable that the whole length of the jig in the range from the bottom surface of the pedestal to the upper end surface of the retaining ring-fitting support is 10 to 100% of the whole length of the rotor.

It is preferable that the pedestal and the retaining ring are uniformly fixedly pressed against the inner surface of the rotor at the upper and lower end positions thereof. Thus it is preferable that both the pedestal and the retaining ring have almost an equal height, namely, 1 to 49% of the whole length of the jig.

The height of the rubber specimen-fitting support is different in dependence on the number of the annular rubber specimens wound around the rubber specimen-fitting support and the like. It is preferable that the height of the rubber specimen-fitting support is in the range of 2 to 98% of the whole length of the jig.

It is preferable that the height of the retaining ring-fitting support is larger than the height of the retaining ring to ensure that the retaining ring can be fixedly fitted on the retaining ring-fitting support. It is preferable that the height of the retaining ring-fitting support is 5 to 95% of the whole length of the jig.

It is preferable that the jig body is formed by integral molding, with axes of the pedestal, the rubber specimen-fitting support, and the retaining ring-fitting support aligned with one another and that the jig body and the retaining ring are made of a material not containing carbon or hydrogen composing an observation nucleus in measuring the solid NMR.

As described above, by aligning the axes of the pedestal, the rubber specimen-fitting support, and the retaining ring-fitting support with one another and aligning these axes with the axis of the rotor rotating at a high speed, the rubber specimen-stretching jig and the annular rubber specimens wound around it are capable of rotating at a high speed in a very stable state.

The jig body having a high strength can be easily manufactured by integrally forming a material into the jig body composed of the pedestal, the rubber specimen-fitting support, and the retaining ring-fitting support, as described above. It is particularly preferable to manufacture the jig body by cutting the material.

As described above, by forming the jig body and the retaining ring from a material, not containing carbon or hydrogen, which composes the observation nucleus in measuring the solid NMR, a 13CNMR spectrum and 1HNMR spectrum of the annular rubber specimen are obtained. Thus the solid NMR can be correctly measured.

It is preferable that the jig body and the retaining ring are made of boron nitride, alumina or zirconium. The jig body and the retaining ring made of the alumina or the zirconium have a high strength and hardness.

It is preferable to form a convexity or a concavity for holding the annular rubber specimen in position on a peripheral surface of the rubber specimen-fitting support.

The above-described construction prevents the annular rubber specimen from shifting from an original position while it is rotating, thus allowing it to rotate in a very stable state.

It is preferable that the annular rubber specimen is wound around the rubber specimen-fitting support perpendicularly to the axial direction thereof, with the left-hand and right-hand sides of the annular rubber specimen being symmetrical with respect to the axis of the rubber specimen-fitting support. But it may be necessary to analyze the property of the annular rubber specimen when it is rotated at a high speed in an inclined state by winding the annular rubber specimen around the rubber specimen-fitting support with the annular rubber specimen inclined at a certain angle to the axial direction of the rubber specimen-fitting support. In this case, the concavity is spirally formed on the peripheral surface of the rubber specimen-fitting support to allow the annular rubber specimen to be rotated at a high speed with the annular rubber specimen wound around the rubber specimen-fitting support at a certain angle to the axial direction thereof.

The second invention provides an apparatus, for analyzing the molecular structure of a stretched rubber specimen and the molecular motion thereof, which has the rubber specimen-stretching jig, wherein the rotor in which the rubber specimen-stretching jig is fixedly fitted is disposed inside a probe for rotating the rubber specimen at a magic angle.

According to a solid NMR apparatus (NMR spectrometer) having the rotor, disposed inside the probe for rotating the specimen at the magic angle, in which the rubber specimen-stretching jig is fixedly fitted and an open portion is closed with a cap, the stretched annular rubber specimen can be rotated at a magic angle. Therefore it is possible to obtain the solid high-resolution NMR spectrum having a sharp peak. That is, it is possible to specify the molecular structure of the stretched annular rubber specimen by obtaining the solid high-resolution NMR spectrum and evaluate the molecular motion thereof by paying attention to the line width of the obtained spectrum.

The third invention provides a method for analyzing a molecular structure of a stretched rubber specimen and a molecular motion thereof, wherein in a state in which a plurality of annular rubber specimens having an identical sectional configuration in a circumferential direction thereof are fixedly wound around a rubber specimen-fitting support of the above-described rubber specimen-stretching jig, with the annular rubber specimens being stretched at not less than 1.1 in an elongation rate thereof, the annular rubber specimens are disposed orthogonally to an axis of the rubber specimen-fitting support with a center of each of the annular rubber specimens disposed coincidentally with the axis of the rubber specimen-fitting support so that a right-hand side and a left-hand side of each of the annular rubber specimens are symmetrical with respect to the axis of the rubber specimen-fitting support.

As described above, the annular rubber specimens having the identical sectional configuration in the circumferential direction thereof are wound around the rubber specimen-fitting support, with each of the annular rubber specimens located on a plane orthogonal to the axis of the rubber specimen-fitting support and with the center of each of the annular rubber specimens coincident with the axis of the rubber specimen-fitting support. Thereby each of the annular rubber specimens is mounted on the rubber specimen-fitting support, with the left-hand and right-hand sides of each of the annular rubber specimens symmetrical with respect to the axis of the rubber specimen-fitting support. By mounting the annular rubber specimens on the rubber specimen-fitting support in this manner, they can be rotated at a high speed in a favorable balance.

It is preferable to set the elongation rate of the annular rubber specimen to not less than 1.1 and particularly preferable to 2 to 8 as described above to obtain the solid NMR spectrum of the stretched annular rubber specimen.

The use of the rubber specimen-stretching jig allows the elongation rate to be changed by altering the number of turns of the annular rubber specimens or winding the annular rubber specimens having different inner diameters around the rubber specimen-fitting support. Thus it is possible to easily obtain the solid NMR spectra of the annular rubber specimens having different elongation rates. Thereby it is possible to compare and investigate the molecular structures and molecular motions of the rubber specimens having different elongation rates.

It is preferable that the rubber specimen-stretching jig is inserted into the rotor, with the annular rubber specimens fixedly wound around the rubber specimen-stretching jig, and the rotor is rotated at a high speed not less than 4 kHz, with the rotor disposed inside a probe for rotating the annular rubber specimens at a magic angle to detect an NMR spectrum.

As described above, by rotating the rotor, disposed inside the probe for rotating the annular rubber specimen at the magic angle, in which the rubber specimen-stretching jig around which the annular rubber specimen is wound is fixedly fitted, it is possible to obtain a sharp high-resolution NMR spectrum of the stretched rubber specimen by removing a chemical shift anisotropy and an interaction of dipoles. Consequently it is possible to analyze the molecular structure of the stretched rubber specimen with high accuracy and easily evaluate the molecular motion thereof by paying attention to the line width of the obtained spectrum.

Normally a blade portion which rotates upon receipt of a jetted gas is formed on the cap of the rotor. The rotor can be rotated at a high speed by closing the open portion of the rotor, with the cap, in which the rubber specimen-stretching jig having the annular rubber specimen wound around it is fixedly fitted and thereafter disposing the rotor inside the probe for rotating the annular rubber specimen at the magic angle to jet a gas from a nozzle of a stator surrounding the rotor inside the probe to the blade portion.

It is particularly preferable to rotate the rotor at a high speed of 0.5 to 15 kHz.

The effect of the present invention is described below. As described above, by so constructing the rubber specimen-stretching jig that the outer surface of the disk-shaped pedestal constructing the jig body and the outer surface of the annular retaining ring fitted around the retaining ring-fitting support constructing the jig body are fixedly pressed against the inner surface of the rotor, it is possible to rotate the rubber specimen-stretching jig at a high speed by interlocking the rubber specimen-stretching jig to the rotor rotating at a high speed.

Before the jig body is inserted into the rotor, by merely winding the annular rubber specimens around the columnar rubber specimen-fitting support erected on the pedestal with the annular rubber specimens being stretched, the annular rubber specimens can be also interlocked to the rotor and rotated in a favorable balance at a high speed, with the annular rubber specimens being stretched uniformly in the rotational direction thereof.

Further the annular rubber specimens can be stably rotated at a high speed by bringing the outer surface of each of the annular rubber specimens wound around the rubber specimen-fitting support into contact with the inner surface of the rotor.

Because the annular rubber specimens wound around the rubber specimen-fitting support are held inside the rotor, it is possible to accomplish a correct temperature-variable measurement by controlling the temperature inside the rotor.

According to the apparatus for analyzing the molecular structure and molecular motion of the stretched rubber specimen, because the stretched annular rubber specimen can be rotated at the magic angle, it is possible to obtain the solid high-resolution NMR spectrum having a sharp peak and specify the molecular structure of the stretched annular rubber specimen and evaluate the molecular motion thereof by paying attention to the line width of the obtained spectrum.

According to the method for analyzing the molecular structure and molecular motion of the stretched rubber specimen, the annular rubber specimen is mounted on the rubber specimen-fitting support, with the left-hand and right-hand sides of the annular rubber specimen symmetrical with respect to the axis of the rubber specimen-fitting support, it can be rotated at a high speed in a favorable balance. Thus it is possible to obtain the solid high-resolution NMR spectrum having a sharp peak. Thereby it is possible to specify the molecular structure of the stretched annular rubber specimen and evaluate the molecular motion thereof.

According to the apparatus and method for analyzing the molecular structure and molecular motion of the stretched rubber specimen, comparison is made between the line width of the 1HNMR, 13CNMR spectrum of a blended elastomer such as natural rubber (NR)/butadiene rubber (BR), natural rubber (NR)/styrene butadiene rubber (SBR), and the like at an unstretched time and the line width thereof at a stretched time to thereby evaluate the molecular motion thereof. Thereby it is possible to clarify to what extent the blended elastomer is tensioned when it is stretched, which contributes to the improvement of the breaking strength thereof and prevention of the generation of cracks.

More specifically, it is possible to know a rolling resistance generated in a tire and its gripping performance to some extent by molding a rubber material into the annular rubber specimen which is mounted on the jig of the present invention with the annular rubber specimen stretched and analyzing the property of the annular rubber specimen rotating at a high speed. Consequently it is possible to form a rubber material having a rolling resistance compatible with its gripping performance, based on the specimen rubber.

According to the apparatus and method for analyzing the molecular structure and molecular motion of the stretched rubber specimen, it is possible to evaluate a stretching-caused change of a crosslinked form of rubber by measuring a 13CNMR spectrum and a 33SNMR spectrum of stretched rubber and analyzing the molecular structure thereof. Thus the apparatus and method for analyzing the molecular structure and molecular motion of the stretched rubber specimen is serviceable for identifying the best vulcanization condition.

BRIEF DESCRIPTION OF THE DRAWINGS

FIG. 7(a) shows a solid high-resolution 13CNMR spectrum of an unstretched (elongation rate α=1) rubber specimen (A); FIG. 7(b) shows a solid high-resolution 13CNMR spectrum obtained in an example 1; FIG. 7(c) shows a solid high-resolution 13CNMR spectrum obtained in an example 2; FIG. 7(d) shows a solid high-resolution 13CNMR spectrum of an unstretched (elongation rate α=1) rubber specimen (B); and FIG. 7(e) shows a solid high-resolution 13CNMR spectrum obtained in an example 3.

DETAILED DESCRIPTION OF THE PREFERRED EMBODIMENTS

The embodiments of the present invention are described below with reference to the drawings.

Figure 2:
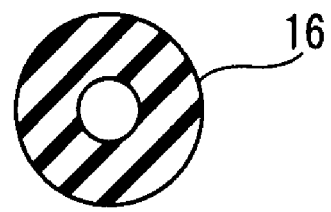
FIG. 2 is a plan view showing an annular rubber specimen.
Figure 3:
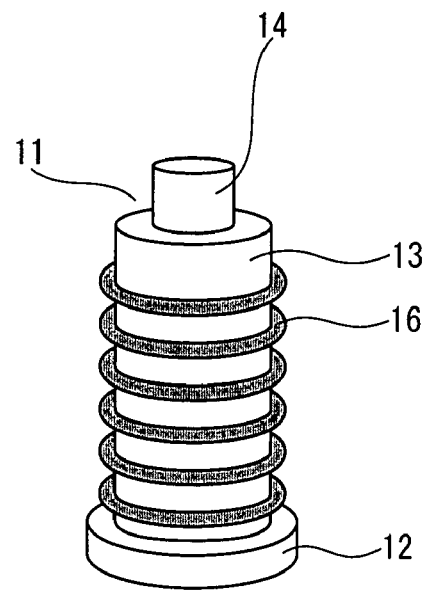
FIG. 3 is a schematic perspective view showing a state in which the annular rubber specimen is wound around the jig body.
Figure 4:
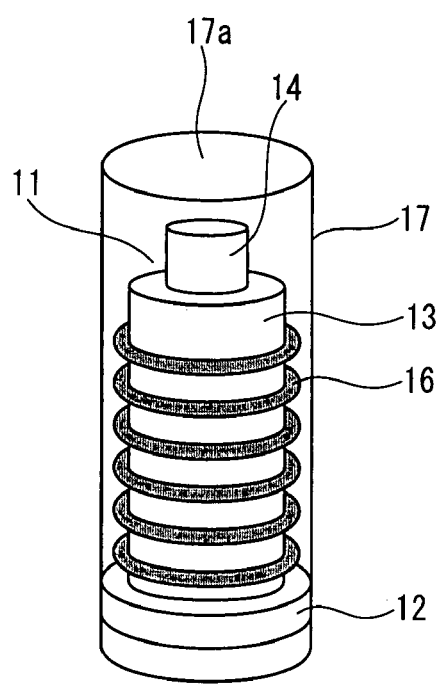
FIG. 4 is a schematic perspective view showing a state in which the jig body around which the annular rubber specimen is wound is inserted into a rotor.
Figure 5:
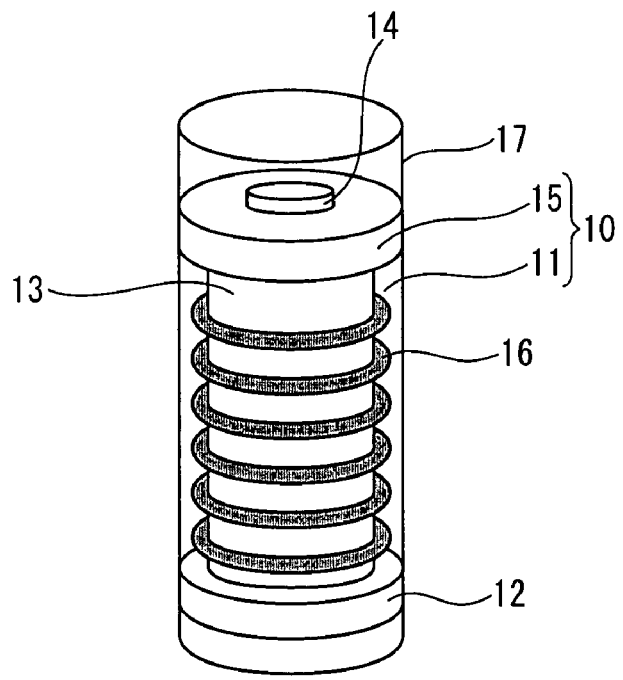
FIG. 5 is a schematic perspective view showing a state in which a retaining ring is fixedly fitted on a retaining ring-fitting support of the jig body inserted into the rotor.

FIGS. 1 through 5 show a rubber specimen-stretching jig of the first embodiment of the present invention. As shown in FIGS. 4 and 5, a rubber specimen-stretching jig 10 around which annular rubber specimens 16 are wound is inserted into a rotor 17 disposed inside a probe (not shown) for rotating the annular rubber specimen at the magic angle of an NMR spectrometer. The rotor 17 (manufactured by Bruker Inc.) used in the first embodiment has an outer diameter of 7 mm, inner diameter of 5.55 mm, and a whole length of 18.0 mm.

Figure 1:
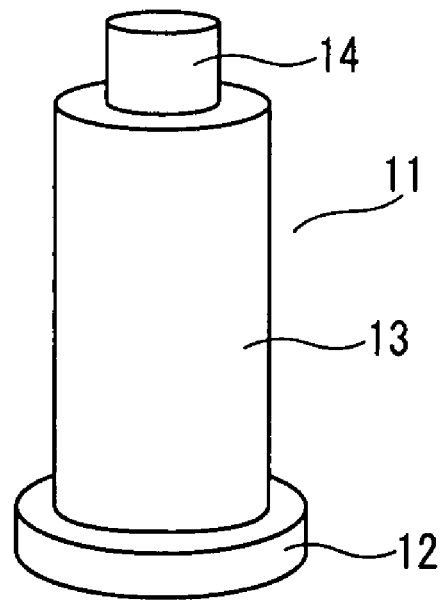
FIG. 1 is a schematic perspective view showing a jig body constructing a rubber specimen-stretching jig of a first embodiment of the present invention.

The rubber specimen-stretching jig 10 has a body 11 and an annular retaining ring 15 those are made of zirconium. As shown in FIG. 1, the body 11 is constructed of a disk-shaped pedestal 12, a columnar rubber specimen-fitting support 13 erected on the pedestal 12, and a columnar retaining ring-fitting support 14 projected from an upper end surface of the rubber specimen-fitting support 13. The jig body 11 is formed by cutting a material, with the axes of the pedestal 12, the columnar rubber specimen-fitting support 13, and the columnar retaining ring-fitting support 14 aligned with one another.

The diameter of the rubber specimen-fitting support 13 is set smaller than that of the pedestal 12. In the first embodiment, the diameter of the pedestal 12 is set to 5.53 mm, whereas the diameter of the rubber specimen-fitting support 13 is set to 4.0 mm (72% of the diameter of the pedestal 12). The diameter of the retaining ring-fitting support 14 is set smaller than that of the rubber specimen-fitting support 13. In the first embodiment, the diameter of the retaining ring-fitting support 14 is set to 3.0 mmm (75% of the diameter of the rubber specimen-fitting support 13).

The whole length of the jig in the range from a bottom surface of the pedestal 12 to an upper end surface of the retaining ring-fitting support 14 is so set that the jig can be accommodated in the rotor 17 and that a cap (not shown) is inserted into the rotor 17 through an open portion 17a thereof by press fit. In the first embodiment, the whole length of the jig is set to 12.5 mm (70% of the diameter of the whole length of rotor). The height of the pedestal 12 is set to 1.5 mm (12% of the whole length of the jig). The height of the rubber specimen-fitting support 13 is set to 8.5 mm (68% of the whole length of the jig). The height of the retaining ring-fitting support 14 is set to 2.5 mm (20% of the whole length of the jig).

The annular retaining ring 15 is fixedly fitted on the retaining ring-fitting support 14 of the body 11 in which the annular rubber specimens 16 are wound around rubber specimen-fitting support 13. In the first embodiment, the outer diameter of the retaining ring 15 is set to 5.53 mm equal to the diameter of the pedestal 12. The inner diameter of the retaining ring 15 is set to 3.0 mm equal to the diameter of the retaining ring-fitting support 14. The height of the retaining ring 15 is set to 1.5 mm equal to the height of the pedestal 12.

The annular rubber specimens 16 shown in FIG. 2 are wound around the rubber specimen-fitting support 13 with the annular rubber specimens 16 stretched. The annular rubber specimens 16 are concentric circles and thus identical to one another in the sectional configurations in the circumferential direction thereof. In the first embodiment, six annular rubber specimens 16 are wound around the rubber specimen-fitting support 13. The annular rubber specimens 16 are sectionally circular (diameter: 1.0 mm) in the circumferential direction thereof. The inner diameter of each of the annular rubber specimens 16 is set to 2.0 mm when it is unstretched. The inner diameter of each unstretched annular rubber specimen 16 is set smaller than the diameter (4.0 mm) of the rubber specimen-fitting support 13 to allow the annular rubber specimen 16 to be stretched even in a single winding. The outer diameter of the annular rubber specimen 16 is set to 4.0 mm.

The method of assembling the rubber specimen-stretching jig of the present invention is described below.

Initially as shown in FIG. 3, six annular rubber specimens 16 are wound around the rubber specimen-fitting support 13 at regular intervals with each of the annular rubber specimens 16 located on a plane orthogonal to the axis of the rubber specimen-fitting support 13 and with the center of each of the annular rubber specimens 16 and the axis of the rubber specimen-fitting support 13 coincident with each other. Thereby each of the annular rubber specimens 16 is mounted on the rubber specimen-fitting support 13, with the left-hand and right-hand sides of the annular rubber specimen 16 symmetrical with respect to the axis of the rubber specimen-fitting support 13. The annular rubber specimen 16 of the first embodiment is so formed that the elongation rate $\alpha$ thereof is 2.0 in a single wounding and 4.0 in a double winding.

Thereafter as shown in FIG. 4, the jig body 11 around which the annular rubber specimens 16 are wound is inserted into the rotor 17 through the open portion 17a thereof. Thereby the outer surface of the pedestal 12 is fixedly pressed against the inner surface of the rotor 17. At this time, the annular rubber specimens 16 wound around the rubber specimen-fitting support 13 contact the inner surface of the rotor 17.

Thereafter as shown in FIG. 5, the retaining ring 15 is fixedly fitted around the retaining ring-fitting support 14, with the outer surface of the retaining ring 15 fixedly pressed against the inner surface of the rotor 17.

After the cap (not shown) having a blade portion provided thereon is inserted into the open portion 17a of the rotor 17, the rotor 17 in which the rubber specimen-stretching jig 10 is fitted is disposed inside the unshown probe for rotating the annular rubber specimen at the magic angle (Bruker Advance 400 manufactured by Bruker Inc.) of the NMR spectrometer. Thereby an apparatus of the present invention for analyzing the molecular structure and the molecular motion of the annular rubber specimen is formed. In this apparatus, while the temperature inside the rotor 17 is being adjusted to 27° C., the rotor 17 is rotated at a high speed of 5.0 kHz to detect a solid high-resolution 13 CNMR spectrum of the stretched annular rubber specimen 16. Thereby the molecular structure and the molecular motion of the annular rubber specimen 16 can be analyzed.

According to the above-described construction, the outer surface of the disk-shaped pedestal 12 which is a part of the jig body 11 and that of the annular retaining ring 15 fixedly fitted on the retaining ring-fitting support 14 are fixedly pressed against the inner surface of the rotor 17. Thus the rubber specimen-stretching jig 10 can be rotated at a high speed by interlocking the rubber specimen-stretching jig 10 to the rotor 17 rotating at a high speed.

Before the jig body 11 is inserted into the rotor 17, by merely winding the annular rubber specimens 16 around the columnar rubber specimen-fitting support 13 erected on the pedestal 12 with the annular rubber specimens 16 being stretched, the annular rubber specimens 16 can be also interlocked to the rotor 17 and can be rotated at a high speed in a favorable balance, with the annular rubber specimens 16 uniformly elongated in the rotational direction thereof.

By bringing the outer surface of each of the annular rubber specimens 16 wound around the rubber specimen-fitting support 13 into contact with the inner surface of the rotor 17, the annular rubber specimens 16 can be rotated stably at a high speed.

Further because the annular rubber specimens 16 wound around the rubber specimen-fitting support 13 are held inside the rotor 17, it is possible to accomplish a correct temperature-variable measurement by controlling the temperature inside the rotor 17.

According to the apparatus, having the above-described construction, for analyzing the molecular structure and molecular motion of the stretched rubber specimen, the stretched annular rubber specimens 16 can be rotated at the magic angle. Thus it is possible to obtain the solid high-resolution 13 CNMR spectrum having a sharp peak. Thereby it is possible to specify the molecular structure of the stretched annular rubber specimen 16 and evaluate the molecular motion thereof by paying attention to the line width of the obtained spectrum.

Further according to the method for analyzing the molecular structure and molecular motion of the stretched rubber specimen, each of the annular rubber specimens 16 is mounted on the rubber specimen-fitting support 13, with the left-hand and right-hand sides thereof symmetrical with respect to the axis of the rubber specimen-fitting support 13. Thus the annular rubber specimens 16 can be rotated at a high speed of not less than 4 kHz in a very favorable balance. Thus it is possible to obtain the solid high-resolution 13 CNMR spectrum having the sharp peak. Thereby it is possible to correctly analyze the molecular structure of the stretched annular rubber specimen 16 and correctly evaluate the molecular motion thereof.

Figure 6:
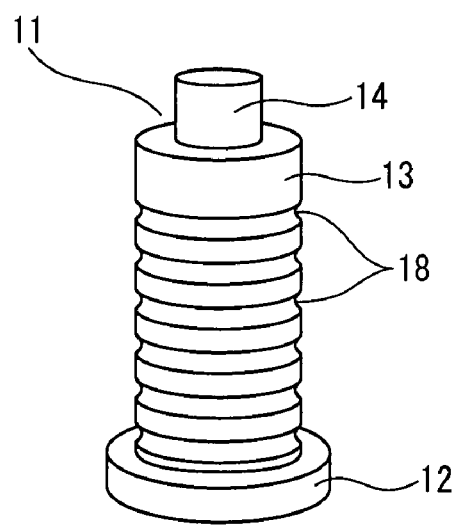
FIG. 6 is a schematic perspective view showing a jig body of a second embodiment having concavities formed on an outer surface of a rubber specimen-fitting support.
Figure 8A:
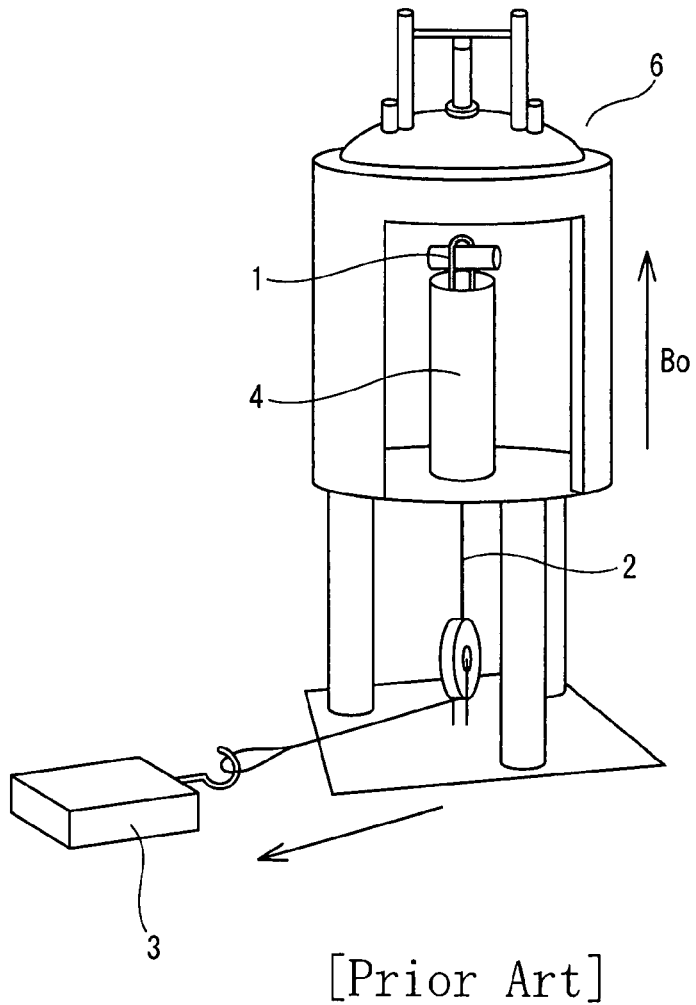
FIG. 8A shows a conventional art.
Figure 8B:
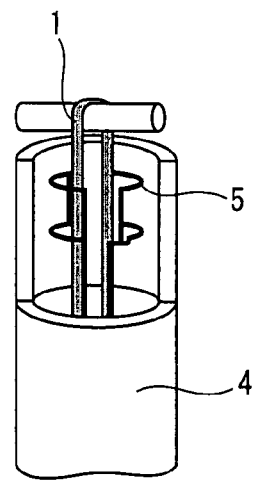
FIG. 8B is an enlarged view showing the inside of a probe.
Figure 9:
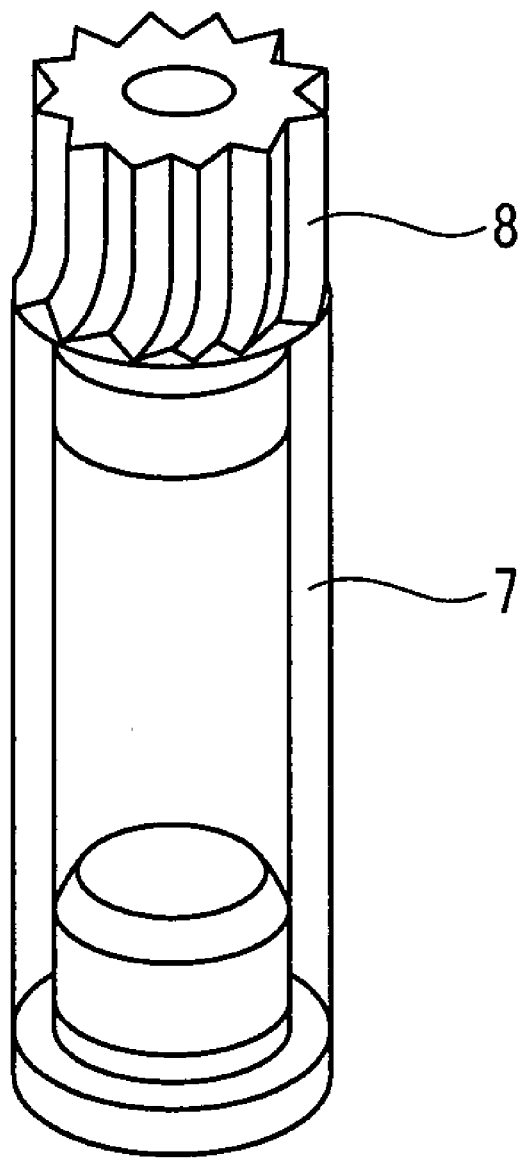
FIG. 9 shows a conventional art.

In the second embodiment, the molecular structure and molecular motion of the stretched rubber specimen are analyzed in a method similar to that of the first embodiment except that as shown in FIG. 6, concavities 18 having circular arc sections 18 are formed at regular intervals to hold the annular rubber specimens to be wound around the rubber specimen-stretching jig 10 in position.

The above-described construction prevents the annular rubber specimen from shifting from an original position during a rotation thereof, thus allowing the annular rubber specimen to rotate at a high speed in a very stable state.

The examples of the present invention are described below.

EXAMPLES 1 THROUGH 3

By using the apparatus, having the above-described construction, for analyzing the molecular structure and molecular motion of the annular rubber specimen, a solid 13CNMR of an annular rubber specimen (A) consisting of natural rubber not containing a reinforcing agent and that of an annular rubber specimen (B) composed of natural rubber and carbon black contained therein as a reinforcing agent were measured. The components of the annular rubber specimens (A) and (B) and the mixing ratio thereof are as shown in table 1. As the vulcanizing condition, the temperature and the period of time were set to 170° C. and 10 minutes respectively.

TABLE 1

|  | Rubber specimen (A) | Rubber specimen (B) |
| --- | --- | --- |
| Natural rubber | 100 | 100 |
| Carbon black | 0 | 30.0 |
| Sulfur | 1.5 | 1.5 |
| Stearic acid | 2.0 | 2.0 |
| Zinc oxide | 3.0 | 3.0 |
| Vulcanization accelerator | 0.5 | 0.5 |

The following agents were used as the components shown in table 1:
Natural rubber: "RSS#3"
Carbon black: "Diablack I (commercial name)" produced by Mitsubishi Chemical Co., Ltd.
Sulfur: "Powdery sulfur (commercial name)" produced by Tsurumi Chemical Industry Co., Ltd.
Stearic acid: "Stearic acid Tsubaki (commercial name)" produced by NOF CORPORATION
Zinc oxide: "Two kinds of zinc oxide (commercial name)" produced by Mitsui Mining and Smelting Co., Ltd.
Vulcanization accelerator: "Nocceler NS (commercial name)" produced by Ouchishinko Chemical Industrial Co., Ltd.

In the example 1, the solid 13CNMR of the annular rubber specimen (A) wound singly around the rubber specimen-fitting support at an elongation rate of $\alpha=2$ was measured. In the example 2, the solid 13CNMR of the annular rubber specimen (A) wound doubly around the rubber specimen-fitting support at an elongation rate of $\alpha=4$ was measured. In the example 3, the solid 13CNMR of the annular rubber specimen (B) wound singly around the rubber specimen-fitting support at an elongation rate of $\alpha=2$ was measured. An irradiated $\pi/2$ pulse width was 4.35 μs. A CP contact period of time was 5 ms. The wait period of time was 6 to 15 s.

FIG. 7 shows the solid high-resolution 13CNMR spectrum obtained in the examples 1 through 3 and the solid high-resolution 13CNMR spectrum of the unstretched (elongation rate $\alpha=1$) rubber specimens (A) and (B).

As apparent from FIG. 7, in the stretched rubber specimens of the examples 1 through 3, the solid high-resolution 13CNMR spectra each having a sharp peak could be obtained. Five peaks corresponding to the chemical structure of cis-1,4 polyisoprene were observed from all the spectra. The positions of the peaks were little changed by the extension of the rubber specimens and the addition of the reinforcing agent to the natural rubber nor the generation of new signals was observed. It is known that the unit's place carbon signal of the polyisoprene is observed in the vicinity of 33 ppm in a cis-conformation and in the vicinity of 44 ppm in a trans-conformation. A change was little observed in the peak intensity of 44 ppm by the elongation of the rubber specimens and the addition of the reinforcing agent to the natural rubber. This suggests that the molecule of the polyisoprene keeps the cis-conformation and does not shift to the trans-conformation, even though the molecule of the polyisoprene is elongated or the reinforcing agent is added to the natural rubber.

The line widths of five peaks of the annular rubber specimens (A) and (B) increase with an increase of the elongation rate. This suggests that the average motion of the rubber molecule decreases by the elongation of the annular rubber specimens (A) and (B).

What is claimed is:

1. A rubber specimen-stretching jig comprising:
a jig body having a disk-shaped pedestal; a columnar rubber specimen-fitting support, erected on said pedestal, whose diameter is smaller than that of said pedestal; and a columnar retaining ring-fitting support, projected from an upper end surface of said rubber specimen-fitting support, whose diameter is smaller than that of said rubber specimen-fitting support; and
an annular retaining ring removably fixedly fitted around said retaining ring-fitting support,
wherein said jig body is inserted into a cylindrical rotor, with one or more stretched annular rubber specimens wound around said rubber specimen-fitting support of said jig body; and with an inner surface of said rotor fixedly pressed against an outer surface of said pedestal and that of said retaining ring and brought into contact with said annular rubber specimens, a solid NMR of each of said annular rubber specimens is measured while said stretched annular rubber specimens are being rotated at a high speed by interlocking said stretched annular rubber specimens to said rotor rotated at a high speed.

2. The rubber specimen-stretching jig according to claim 1, wherein said jig body is formed by integral molding, with axes of said pedestal, said rubber specimen-fitting support, and said retaining ring-fitting support aligned with one another; and said jig body and said retaining ring are made of a material not containing carbon or hydrogen composing an observation nucleus in measuring a solid NMR.

3. The rubber specimen-stretching jig according to claim 2, wherein said material consists of alumina or zirconium.

4. The rubber specimen-stretching jig according to claim 1, wherein a convexity or a concavity for holding an annular rubber specimen in position is formed on a peripheral surface of said rubber specimen-fitting support.

5. An apparatus, for analyzing a molecular structure of a stretched rubber specimen and a molecular motion thereof, comprising a rubber specimen-stretching jig according to claim 1, wherein a rotor in which said rubber specimen-stretching jig is fixedly fitted is disposed inside a probe for rotating said rubber specimen at a magic angle.

6. A method for analyzing a molecular structure of a stretched rubber specimen and a molecular motion thereof, wherein in a state in which a plurality of annular rubber specimens having an identical sectional configuration in a circumferential direction thereof are fixedly wound around a rubber specimen-fitting support of a rubber specimen-stretching jig according to claim 1, with said annular rubber specimens being stretched at not less than 1.1 at an elongation rate thereof, said annular rubber specimens are disposed orthogonally to an axis of said rubber specimen-fitting support with a center of each of said annular rubber specimens disposed coincidentally with said axis of said rubber specimen-fitting support so that a right-hand side and a left-hand side of each of said annular rubber specimens are symmetrical with respect to said axis of said rubber specimen-fitting support.

7. The method according to claim 6, wherein said rubber specimen-stretching jig is inserted into said rotor, with said annular rubber specimens fixedly wound around said rubber specimen-stretching jig, and said rotor is rotated at a high speed not less than 4 kHz, with said rotor disposed inside a probe for rotating said annular rubber specimens at a magic angle to detect an NMR spectrum.

* * * * *